United States Patent
Goodsitt et al.

(10) Patent No.: US 10,314,477 B1
(45) Date of Patent: Jun. 11, 2019

(54) SYSTEMS AND METHODS FOR DYNAMICALLY MODIFYING VISUAL CONTENT TO ACCOUNT FOR USER VISUAL IMPAIRMENT

(71) Applicant: Capital One Services, LLC, McLean, VA (US)

(72) Inventors: Jeremy Goodsitt, Champaign, IL (US); Anh Truong, Champaign, IL (US); Mark Watson, Urbana, IL (US); Fardin Abdi Taghi Abad, Champaign, IL (US); Reza Farivar, Champaign, IL (US); Austin Walters, Savoy, IL (US)

(73) Assignee: CAPITAL ONE SERVICES, LLC, McLean, VA (US)

( * ) Notice: Subject to any disclaimer, the term of this patent is extended or adjusted under 35 U.S.C. 154(b) by 0 days.

(21) Appl. No.: 16/176,985

(22) Filed: Oct. 31, 2018

(51) Int. Cl.
    *G06F 16/2457*    (2019.01)
    *A61B 3/06*    (2006.01)
    *G06N 3/08*    (2006.01)

(52) U.S. Cl.
    CPC .......... *A61B 3/066* (2013.01); *G06F 16/2457* (2019.01); *G06N 3/08* (2013.01)

(58) Field of Classification Search
    CPC ........................... G06F 16/2457; A61B 3/066
    See application file for complete search history.

(56) References Cited

U.S. PATENT DOCUMENTS

| | | | |
|---|---|---|---|
| 5,267,331 A | 11/1993 | Siwoff | |
| 2006/0209258 A1* | 9/2006 | Nareppa | A61B 3/066 351/242 |
| 2017/0351952 A1 | 12/2017 | Zhang et al. | |
| 2017/0358274 A1* | 12/2017 | Garcia | G06F 3/0481 |
| 2018/0075581 A1 | 3/2018 | Shi et al. | |
| 2018/0122048 A1 | 5/2018 | Wang et al. | |

FOREIGN PATENT DOCUMENTS

WO      2017162980      9/2017

OTHER PUBLICATIONS

Gatys, L.A. et al.; "A Neural Algorithm of Artistic Style", Werner Reichardt Centre for Integrative Neuroscience . . . , arXiv:1508.06576v2 [cs.CV] Sep. 2, 2015.

Johnson, J. et al.; "Perceptual Losses for Real-Time Style Transfer and Super-Resolution", Department of Computer Science, Stanford University, arXiv:1603.08155v1 [cs.CV] Mar. 27, 2016.

Pfau, D. et al.; "Conneting Generative Adversarial Networks and Actor-Critic Methods", Google DeepMind, arXiv:1610.01945v3 [cs.LG] Jan. 18, 2017.

Zhu, J. et al.; "Unpaired Image-to-Image Translation using Cycle-Consistent Adversarial Networks", Berkeley AI Research (BAIR) laboratory, UC Berkeley; arXiv:1703.10593v4 [cs.CV] Feb. 19, 2018.

* cited by examiner

*Primary Examiner* — Antonio A Caschera
(74) *Attorney, Agent, or Firm* — Hunton Andrews Kurth LLP

(57) ABSTRACT

Systems and methods of dynamically modifying visual content to account for user visual impairments utilize a plurality of generative adversarial networks. Each of the plurality of generative adversarial networks are associated with a corresponding style transfer, wherein the style transfer uniquely transforms the color mapping of a content template based on responses to at least one visual impairment test.

19 Claims, 5 Drawing Sheets

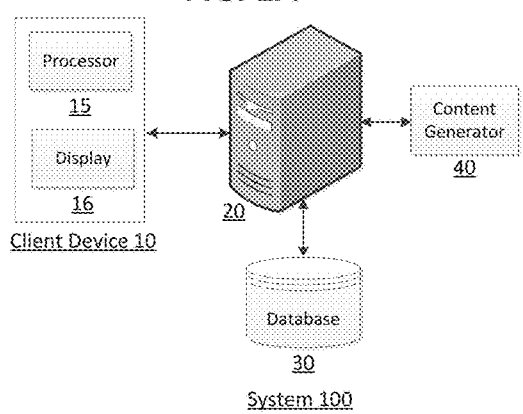
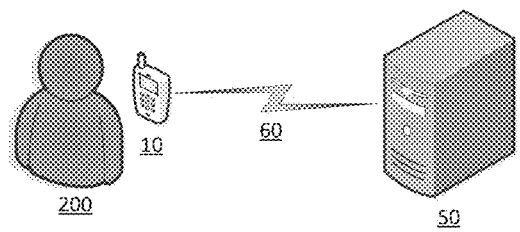
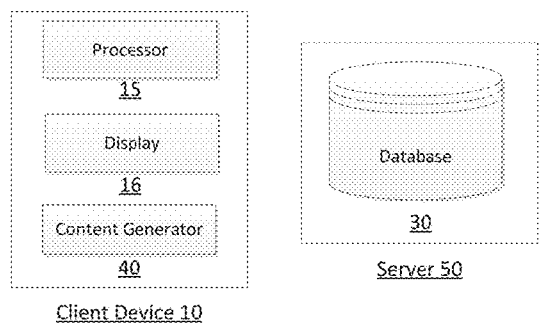
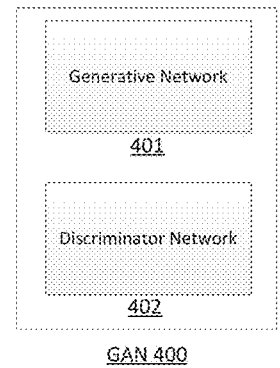

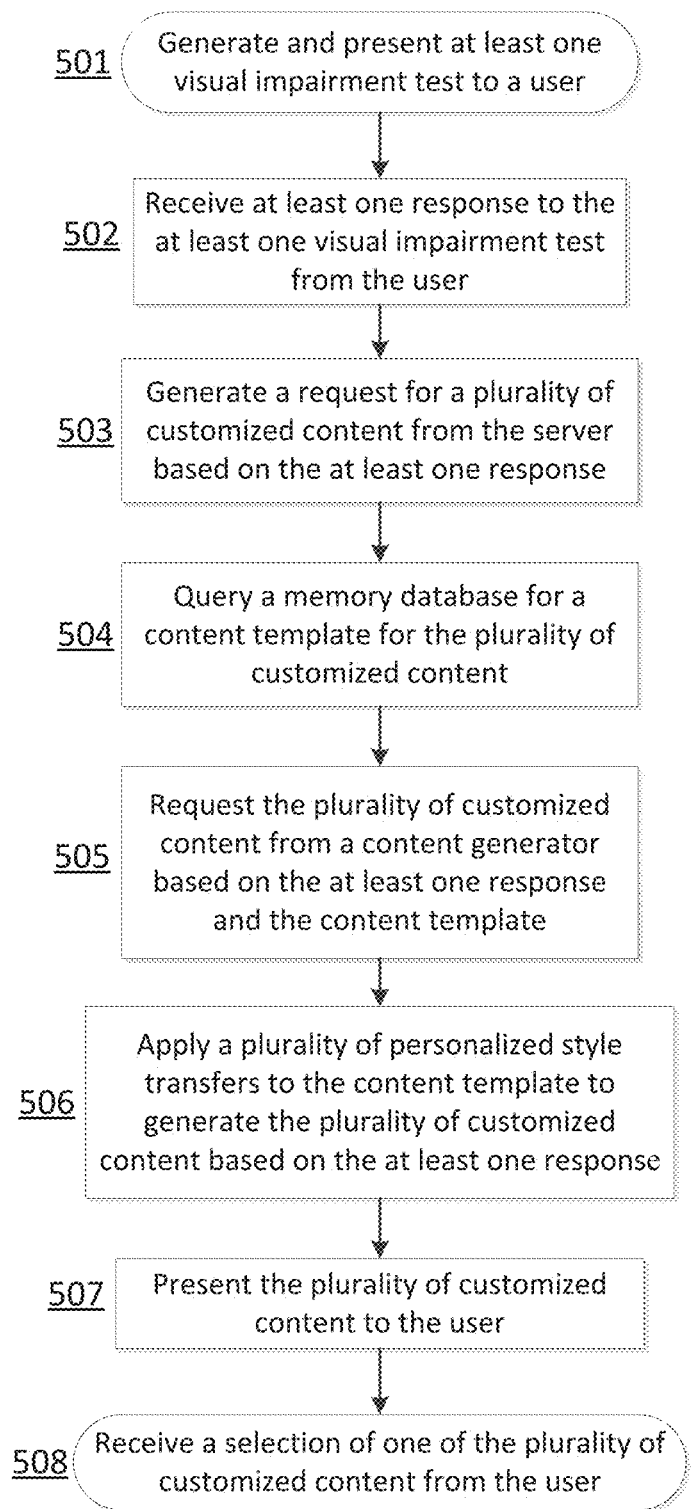

SYSTEMS AND METHODS FOR DYNAMICALLY MODIFYING VISUAL CONTENT TO ACCOUNT FOR USER VISUAL IMPAIRMENT

TECHNICAL FIELD

The present application relates to systems and methods for dynamically modifying visual content to account for user visual impairments.

BACKGROUND

Visual impairments such as color blindness affect many people. Color blindness is a color vision deficiency that prevents people from distinguishing certain types of colors. There are three main types of color blindness: red-green color blindness (i.e., person can't distinguish between the colors red and green), blue-yellow color blindness (i.e., person can't distinguish between the colors blue and yellow), and complete color blindness (i.e., person can't experience any type of color). Color blindness can be diagnosed by testing the particular type of color blindness. For example, a red-green color blindness test would consist of the colors red and green, a blue-yellow color blindness test would consist of the colors blue and yellow, and a complete color blindness test would consist of a variety of different colors. A person with normal color vision will be able to distinguish the particular colors in the tests, while a person with color blindness would not. Unfortunately, however, many of the currently-generated visual content (e.g., images and videos) do not take into consideration people with color blindness. As such, people with color blindness aren't able to appreciate such content as someone with normal color vision might. Further, once the visual content is generated, there is currently no means of modifying the content to account for such visual impairments.

Accordingly, there is a need for dynamically modifying visual content to account for visual impairments like color blindness.

BRIEF DESCRIPTION OF THE DRAWINGS

FIG. 1A illustrates an example embodiment of a system employing dynamic modification of visual content.

FIG. 1B illustrates another example embodiment of a system employing dynamic modification of visual content.

FIG. 1C illustrates an example embodiment of the client device and server depicted in FIG. 1B.

FIG. 1D illustrates an example embodiment of a generative adversarial network.

FIG. 4 illustrates an example embodiment of a method for dynamically modifying visual content.

DESCRIPTION OF EMBODIMENTS

Figure 2A:
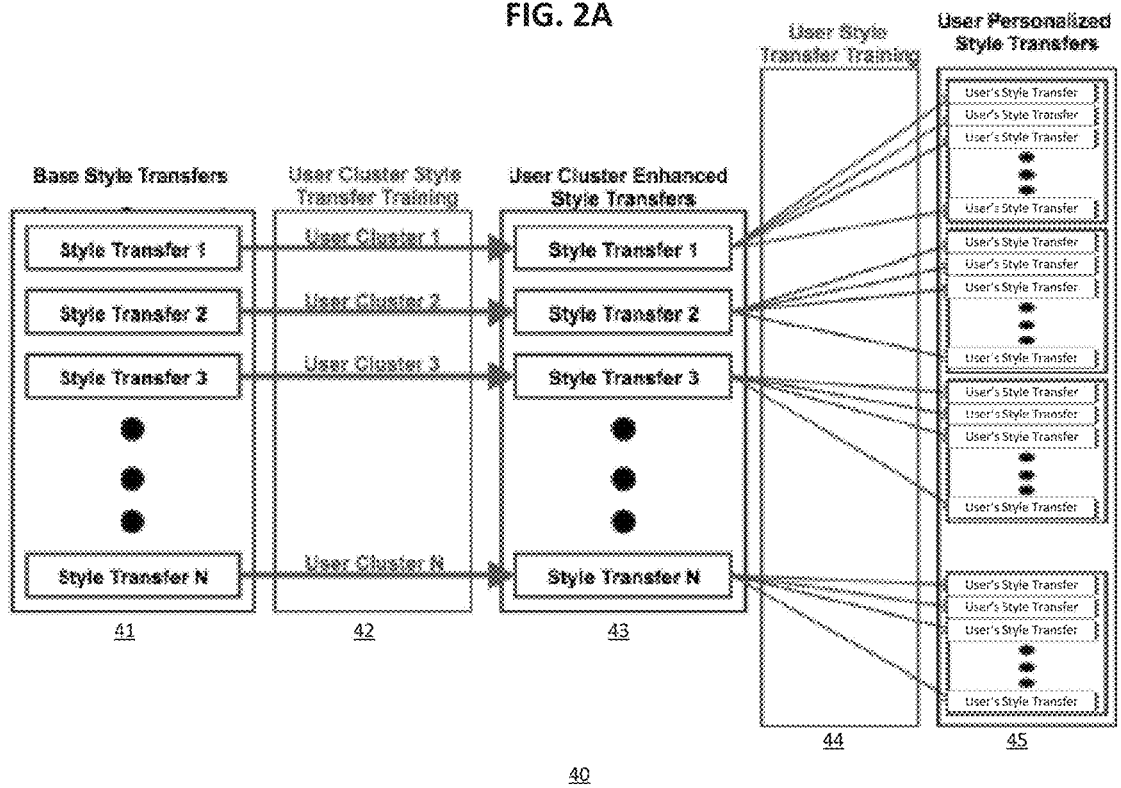
FIG. 2A illustrates an example embodiment of a flow diagram for training a plurality of style transfers.

The following description of embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

One aspect of the present disclosure is to provide a system and method for dynamically modifying visual content. The systems and methods herein address at least one of the problems discussed above.

According to an embodiment, a system for dynamically modifying visual content includes: a processor; a server; a memory database; and a content generator, wherein the content generator includes a plurality of generative adversarial networks, wherein each generative adversarial network is associated with at least one corresponding style transfer; wherein: (i) the processor is configured to: generate and present at least one visual impairment test to a user, receive at least one response to the at least one visual impairment test from the user, and generate a request for a plurality of customized content from the server based on the at least one response; (ii) the server is configured to: query the memory database for a content template for the plurality of customized content, and request the plurality of customized content from the content generator based on the at least one response and the content template; (iii) the content generator is configured to apply a plurality of personalized style transfers to the content template to generate the plurality of customized content based on the at least one response; and (iv) the processor is further configured to: present the plurality of customized content to the user, and receive a selection of one of the plurality of customized content from the user.

According to an embodiment, a method for dynamically modifying visual content includes: generating and presenting, with a processor, at least one visual impairment test to a user; receiving, with the processor, at least one response to the at least one visual impairment test from the user; generating, with the processor, a request for a plurality of customized content from the server based on the at least on response; querying, with a server, a memory database for a content template for the plurality of customized content; requesting, with the server, the plurality of customized content from a content generator based on the at least one response and the content template; applying, at the content generator, a plurality of personalized style transfers to the content template to generate the plurality of customized content based on the at least one response; presenting, with the processor, the plurality of customized content to the user; receiving, with the processor, a selection of one of the plurality of customized content from the user.

According to an embodiment, a system for dynamically modifying visual content includes a mobile device and a server, wherein the mobile device includes a processor, wherein the processor is configured: generate and present at least one visual impairment test to a user, receive at least one response to the at least one visual impairment test from the user, and generate a request for a plurality of customized content from the server based on the at least one response; wherein the server includes a plurality of generative adversarial networks, wherein each generative adversarial network is associated with at least one corresponding style transfer, wherein the server is configured to apply a plurality of personalized style transfers to a content template to generate the plurality of customized content based on the at least one response.

FIG. 1A illustrates an example embodiment of a system employing dynamic modification of visual content. In an embodiment, as depicted in the figure, a system 100 includes a client device 10, a server 20, a database 30, and a content generator 40. In an embodiment, the client device 10 may be a mobile device, e.g., smart phone, tablet, personal computer, etc. The client device 10 may include a processor 15. In an embodiment, the processor 15 is suitable for the execution of a computer program and may include, by way of example, both general and special purpose microprocessors, and any one or more processors of any kind of digital computer. Further, the client device 10 is configured to receive specific user input. For example, the client device 10 may be configured to access and browse content such as a website, a television channel, or a video game. Further, in an embodiment, after the user accesses said content, the client device 10 may provide additional content to the user, e.g., a visual impairment test. The additional content may be activated automatically by the client device 10 (e.g., via the processor 15). In another embodiment, the additional content may be activated intentionally by the user (e.g., by intentionally initiating the additional content on the client device 10). In particular, in an embodiment, the processor 15 is configured to: generate and present at least one visual impairment test to a user, receive at least one response to the at least one visual impairment test from the user, and generate a request for a plurality of customized content from the server 20 based on the visual impairment test response. Further, in an embodiment, the visual impairment test may be provided to the user via a display 16 and speakers. In an embodiment, the display may be a liquid crystal display (LCD), e.g., thin-film-transistor (TFT) LCD, in-place switching (IPS) LCD, capacitive or resistive touchscreen LCD, etc. Further, the display 16 may also be an organic light emitting diode (OLED), e.g., active-matrix organic light emitting diode (AMOLED), super AMOLED, etc. Further, the server 20 may be a back-end component and may be configured to interact with each of the client device 10, the database 30, and the content generator 40 to provide generated content to display 16 at the client device 10. For example, the server 20 may receive the request for the plurality of customized content from the client device 10, query the memory database 30 for a content template, and request the plurality of customized content from the content generator 40 based on the visual impairment test response and the content template. In an embodiment, the content generator 40 is configured to: compare the visual impairment test response to a plurality of clustered style transfers, identify one of the plurality of clustered style transfers based on the comparison, generate the plurality of personalized style transfers based on the identification, and apply the plurality of personalized style transfers to the content template to generate the plurality of customized content. Further, the server 20 is also configured to: receive the receive the generated customized content from the content generator 40, and then transmit the generated customized content to the client device 10, where the generated customized content is presented to the user for selection. In an embodiment, the memory database 30 is configured to store a plurality of content templates to be used in generating the additional content with the content generator 40. In an embodiment, the content template may be a live-action video. In another embodiment, the content template may be a bare-bones image. For example, the content template may be an image that only includes stick figures. In an embodiment, the style transfers may transform the color palette scheme of the content template. As such, for people with red-green or blue-yellow color blindness, the style transfer may transform that content template such that the colors are easier to distinguish. In an embodiment, each of the style transfers is trained with a distinct pre-built model. Specifically, each of the style transfers are trained with distinct generative adversarial networks (GANs). In an embodiment, a GAN includes a generative network and a discriminator network. In an embodiment, the generative network creates new content and the discriminator network determines if the content generated by the generative network is a real image or the generated content. After a period of time, the generative network is able to generate content that can deceive the discriminator network into determining that the generated content is a real image. In an embodiment, the content determined to be real is then output to be provided back to the client device 10. In an embodiment, the GAN can be trained on paired or unpaired data. In a paired dataset, every inputted image (e.g., content template) is manually mapped to an image in a target domain (e.g., content template with corrected color palette scheme). Therefore, with a paired dataset, the generative network takes an input and maps the input image to an output image, which must be close to its mapped counterpart. However, with unpaired datasets, a cycle-consistent GAN may be utilized. With cycle-consistent GANs, after a first generative network transforms a given image from a first domain (e.g., content template) to a target domain (e.g., corrected content template), a second generative network then transforms the newly generated image from the target domain to the first domain. By transforming the generated image from the target domain to the first domain, a meaningful mapping between the input and output images can be defined for unpaired datasets.

FIG. 1B illustrates another example embodiment of a system employing dynamic modification of visual content. In an embodiment, FIG. 1B depicts a user 200 using the client device 10 as well as a server 50. In an embodiment, the client device 10 may communicate with the server 50 by any form or medium of digital data communication, e.g., a communication network 60. Examples of a communication network 60 include a local area network (LAN) and a wide area network (WAN), e.g., the Internet. In an embodiment, the server 50 is similar to server 20 except that it also includes the database 30 and the content generator 40 as depicted in FIG. 1C. In addition, as also depicted in FIG. 1C, the client device 10 may also include the content generator 40.

FIG. 1D illustrates an example embodiment of a generative adversarial network. As depicted in the figure, a GAN 400 includes a generative network 401 and a discriminator network 402. As described above, the generative network 401 creates new content and the discriminator network 402 determines if the content generated by the generative network 401 is a real image or the generated content. Further, after a period of time, the generative network 401 is able to generate content that can deceive the discriminator network 402 into determining that the generated content is a real image.

FIG. 2A illustrates an example embodiment of a flow diagram for training a plurality of style transfers. As depicted in the figure, the content generator 40 begins with a plurality of base style transfers 1 to N, i.e., style transfers 41. As described above, each of the base style transfers 41 may correspond to a particular color mapping, wherein each base style transfer 41 may uniquely transform the color palette scheme of a particular content template. In an embodiment, the base style transfer 41 may be trained on a large sample of people (e.g., several hundred) with different degrees of color blindness and visual impairments. In particular, each of the base style transfers 41 are trained with a corresponding cluster of users 42. In an embodiment, each cluster of users 42 may correspond to a particular degree and/or type of color blindness and other visual impairments, which may be determined based on those users' responses to a variety of visual impairment tests. For example, a first user cluster 42 may correspond to users with red-green colorblindness, while a second user cluster 42 may correspond to users with blue-yellow colorblindness. As such, the first user cluster 42 may correspond to a base style transfer 41, e.g., style transfer 1, with a color mapping that better distinguishes the colors red and green. Similarly, the second user cluster 42 may correspond to a base style transfer 42, e.g., base style transfer 2, with a color mapping that better distinguishes the colors blue and yellow. Further, the other base style transfers may correspond to different degrees of the red-green color blindness and the blue-yellow color blindness, respectively. Accordingly, by training the base style transfers 41 with their corresponding user clusters 42, the base style transfers 41 may be made more accurate as depicted by the user cluster enhanced style transfers 43. Then, each of the enhanced style transfers 43 may be further personalized, e.g., user personalized style transfers 45, based on additional training 44 using a particular user's responses to visual impairment tests. In particular, the training generates a plurality of user personalized style transfers 45 that are associated with each of the enhanced style transfers 43, thereby providing an ability for the user to select the best style transfer out of a variety of different options. For example, as regards to style transfer 1 of the enhanced style transfers 43, which may be associated with red-green color blindness, each of the corresponding generated user personalized style transfers 45 may apply a slightly distinct color mapping to a content template to account for the red-green color blindness. Similarly, as regards to style transfer 2 of the enhanced style transfers 43, which may be associated with blue-yellow color blindness, each of the corresponding generated user personalized style transfers 45 may apply a slightly distinct color mapping to a content template to account for the blue-yellow color blindness. In an embodiment, each of the style transfers 1 to N of the base style transfers 41 are associated with a distinct GAN. However, in another embodiment, each of the style transfers 1 to N of the base style transfers 41 can be associated with multiple GANs. In other words, a particular style transfer can be composed of a series of other style transfers. Further, in an embodiment, the GAN (or GANs) associated with each of the base style transfers 41 also performs the user cluster training 42 and the additional personalized training 44 to generate the enhanced style transfers 43 and the personalized style transfers 45, respectively. The user cluster training 42 and the additional personalized training 44 are performed in a similar manner. For example, the user cluster training 42 utilizes the base style transfers 41 as a starting state, while the additional personalized training 44 utilizes the enhanced style transfers 43. Further, the base style transfers 41 and the enhanced style transfers 43 have corresponding sets of weights which are used as initial values for the weights when performing either the user cluster training 42 or the additional personalized training 44, respectively. In an embodiment, the user cluster training 42 is performed based on inputs from the clusters of users, while the additional personalized training 44 is performed based on inputs from an individual user. In particular, during the user cluster training 42, training is conducted on the images selected by the cluster(s) of users as being better than other presented images, i.e., positive reinforcement. Further, in an embodiment, the training is iterated until (i) a predefined number of iterations is reached, (ii) the enhanced style transfers 43 have ceased improving, or (iii) the cluster of users determine that the enhanced style transfers 43 are good enough. Further, during the additional personalized training 44, training is conducted on the images selected by the user as being better than another image. In addition, similar to the user cluster training 42, the training is iterated until (i) a predefined number of iterations is reached, (ii) the personalized style transfers 45 have ceased improving, or (iii) the user determines that the personalized style transfers 45 are good enough.

Figure 2B:
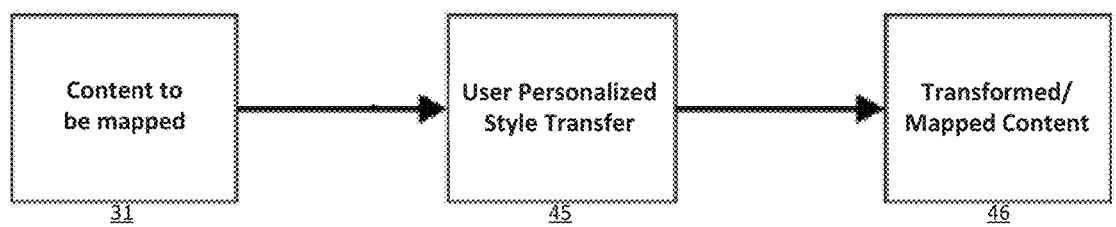
FIG. 2B illustrates an example embodiment of a flow diagram for applying a user personalized style transfer to a content template.

FIG. 2B illustrates an example embodiment of a flow diagram for applying a user personalized style transfer to a content template. As depicted in the figure, a user personalized personal style transfer 45 is applied to a content template 31 to generate corrected content 46. In an embodiment, the content template 31 can be a video or an image. If the content template 31 is an image, a style transfer is applied to that individual image. However, if the content template 31 is a video, the style transfer may be applied to each individual video frame of the content template 31. For example, the style transfer can be applied to each video frame consecutively. However, in another embodiment, the style transfer can be applied simultaneously to a number of video frames. For example, in an embodiment, because each frame transformation image can be considered independent of the other image transformation processes within the video, if multiple parallel systems are running with the same style transfer, each individual frame can be processed in parallel.

Figure 2C:
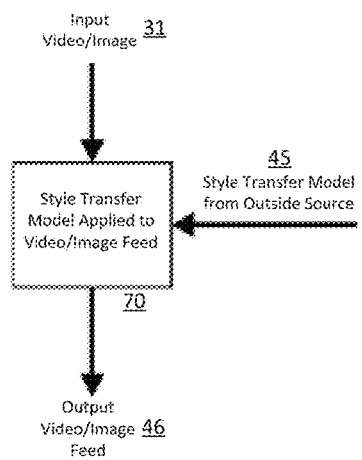
FIG. 2C illustrates an example embodiment of a device incorporating the mapping process depicted in FIG. 2B.

FIG. 2C illustrates an example embodiment of a device incorporating the mapping process depicted in FIG. 2B. In an embodiment, a hardware device 70 is configured to receive a feed of the content template 31 and then apply a user personalized style transfer 45 to the content template in order to generate the corrected customized content 46. Further, in an embodiment, the user personalized style transfer 45 may be retrieved from an outside source via at least one of a universal serial bus (USB), WiFi, LAN, WAN, Bluetooth, etc.

Figure 3A:
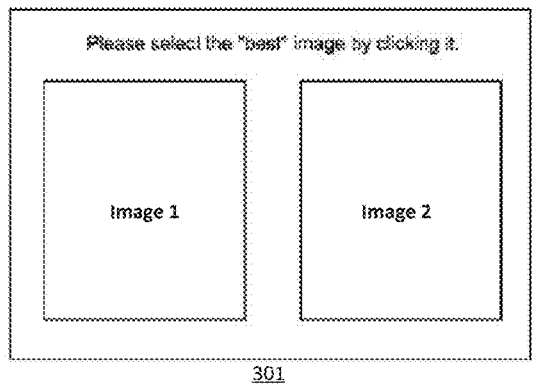
FIG. 3A illustrates an example embodiment of a visual impairment test.

FIG. 3A illustrates an example embodiment of a visual impairment test. As depicted in the figure, in visual impairment test 301, a user is required to select, i.e., by clicking, the "best" of two presented images, e.g., image 1 and image 2. In an embodiment, images 1 and 2 may correspond to the same image with different color mappings. For example, assuming the visual impairment red-green color blindness, image 1 may correspond to an image with a first color mapping, while image 2 may correspond to the same image with a second color mapping. Accordingly, based on a selected image, the severity of the color blindness can be determined. In another embodiment, images 1 and 2 may correspond to different images. Further, the visual impairment test 301 can also present more than two images.

Figure 3C:
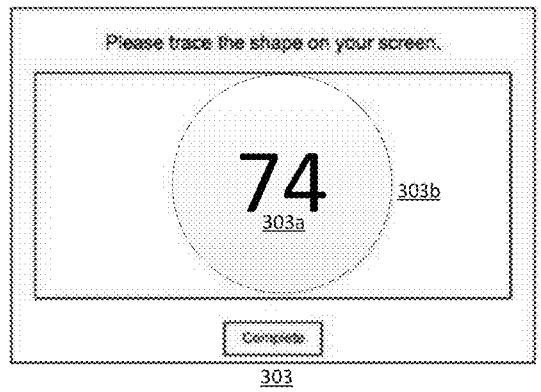
FIG. 3C illustrates another example embodiment of a visual impairment test.
Figure 3B:
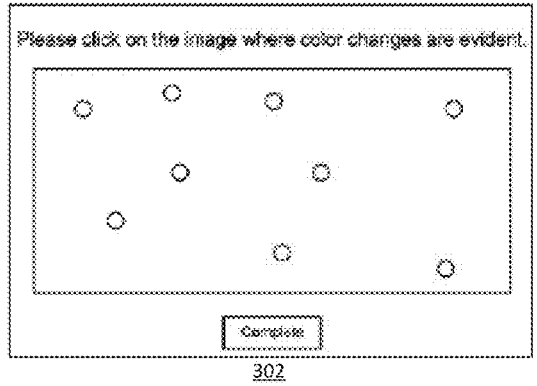
FIG. 3B illustrates another example embodiment of a visual impairment test.

FIG. 3B illustrates another example embodiment of a visual impairment test. In an embodiment, in visual impairment test 302, the user is required to select (i.e., click) at least one image where color change is evident. The color change can be between any two colors along the color spectrum. In an embodiment, the at least one image may include a plurality of Ishihara plates, i.e., dots appearing randomized in color and size. Accordingly, red-green color blindness can be tested by determining if the user can see the transition between a red-like color and a green-like color (and vice-versa), and blue-yellow color blindness can be tested by determining if the user can see the transition between a blue-like color and a yellow-like color (and vice versa). Specifically, if the user does not select the image with a red-green transition or a blue-yellow transition, then it is likely that the user has either red-green color blindness or blue-yellow color blindness, respectively. In an embodiment, at least one of the images may have no color changes, i.e., the image displays a static color. Further, as depicted in the figures, the images may be circular. However, in another embodiment, the images may correspond to different shapes. Further, after the user is finished selecting the desired images, the "complete" button may be selected to exit out of the test.

FIG. 3C illustrates another example embodiment of a visual impairment test. In an embodiment, in visual impairment test 303, the user is required trace the shape of an image 303a in a plate 303b. In an embodiment, the image 303a may correspond to a first color of the red-green (or blue-yellow) color blindness, and the area within the plate 303b may correspond to a second color of the red-green (or blue-yellow) color blindness. Further, as depicted in the figure, the image 303a is associated with the number "74." Further, in an embodiment, the image 303a and the area within the plate 303b may include a plurality of Ishihara plates. After the user is finished tracing the image 303a, the "complete" button may be selected to exit out of the test.

Figure 3D:
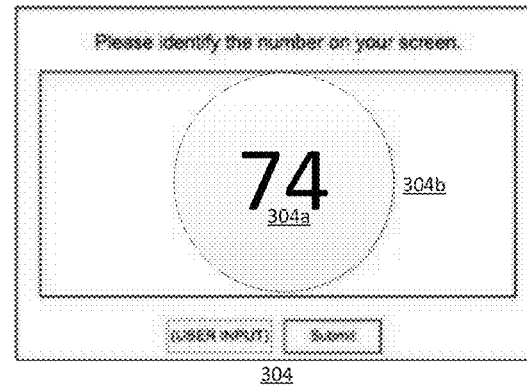
FIG. 3D illustrates another example embodiment of a visual impairment test.

FIG. 3D illustrates another example embodiment of a visual impairment test. In an embodiment, visual impairment test 304, which includes an image 304a in a plate 304b, is similar to the visual impairment test 303 except that instead of tracing the image 304a, the user has to input the number associated with the image 304a, e.g., "74." Further, after the user inputs the number associated with the image 304a, the user may then select the "submit" button to exit out of the test.

FIG. 4 illustrates an example embodiment of a method for dynamically modifying visual content. As depicted in the figure, in a first step 501, at least one visual impairment test is generated and presented to a user. For example, at least one of visual impairment tests 301 to 304 may be generated and presented to the user, by the processor 15, at a client device 10. In an embodiment, different variations of the same visual impairment test may be presented to the user. Then, in step 502, the client device 10 receives responses to the at least one visual impairment test. In step 503, the client device 10 generates a request for a plurality of customized content 46 from the server 20 (or the server 50) based on the response(s) to the visual impairment test(s). In response to the request from the client device 10, the server 20/50 then queries the memory database 30 for a content template 31 as depicted in step 504. As described above, the content template 31 may be one of a video or image. Then, in step 505, the server 20/50 requests the plurality of customized content 46 from a content generator 40 based on the at least one visual impairment test response and the content template 31. The content generator 40 then applies a plurality of personalized style transfers 45 to the content template 31 to generate the plurality of customized content 46 based on the at least one visual impairment test response, in step 506. For example, if the visual impairment test responses indicated that the user has a certain level of red-green color blindness, the applied personalized style transfer 45 would correspond to a color mapping that would account for that level of red-green color blindness. Further, as described above, the plurality of the personalized style transfers may be generated by training (i.e., with the GANs at the content generator 40) the enhanced style transfers 43 on the user's visual impairment test responses. Then, in step 507, the generated plurality of customized content 46 is transmitted to the processor 15, where it is presented to the user for selection. Accordingly, in step 508, the processor 15 may receive the selection of one of the plurality of customized content 46 from the user. As such, the user may interact with content 46 that best addresses (i.e., corrects for) their type of visual impairment. Further, in another embodiment, the selected one of the plurality of customized content 46 may be transmitted to at least one other device. Further, in an embodiment, the personalized style transfer 45 associated with the selected one of the plurality of customized content 46 may be applied to other visual content at the client device. In particular, the processor 15 may activate the application of aforementioned personalized style transfer 45. As such, whenever the user interacts with other content, the personalized style transfer 45 may be applied to the content to account for the user's particular visual impairment.

Implementations of the various techniques described herein may be implemented in digital electronic circuitry, or in computer hardware, firmware, software, or in combinations of them. Implementations may be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application specific integrated circuit).

In the foregoing Description of Embodiments, various features may be grouped together in a single embodiment for purposes of streamlining the disclosure. This method of disclosure is not to be interpreted as reflecting an intention that the claims require more features than are expressly recited in each claim. Rather, as the following claims reflect, inventive aspects lie in less than all features of a single foregoing disclosed embodiment. Thus, the following claims are hereby incorporated into this Description of Embodiments, with each claim standing on its own as a separate embodiment of the invention.

Moreover, it will be apparent to those skilled in the art from consideration of the specification and practice of the present disclosure that various modifications and variations can be made to the disclosed systems without departing from the scope of the disclosure, as claimed. Thus, it is intended that the specification and examples be considered as exemplary only, with a true scope of the present disclosure being indicated by the following claims and their equivalents.

The invention claimed is:

1. A system for dynamically modifying visual content, the system comprising:
 a processor;
 a server;
 a memory database; and
 a content generator, wherein the content generator includes a plurality of generative adversarial networks, wherein each generative adversarial network is associated with at least one corresponding style transfer;
 wherein:
 the processor is configured to:
 generate and present at least one visual impairment test to a user,
 receive at least one response to the at least one visual impairment test from the user, and
 generate a request for a plurality of customized content from the server based on the at least one response;
 the server is configured to:
 query the memory database for a content template for the plurality of customized content, and
 request the plurality of customized content from the content generator based on the at least one response and the content template;
 the content generator is configured to apply a plurality of personalized style transfers to the content template to generate the plurality of customized content based on the at least one response; and
 the processor is further configured to:
 present the plurality of customized content to the user, and
 receive a selection of one of the plurality of customized content from the user.

2. The system of claim 1, wherein the content generator is further configured to:
 compare the at least one response to a plurality of clustered style transfers,
 identify one of the plurality of clustered style transfers based on the comparison,
 generate the plurality of personalized style transfers based on the identification, and
 apply the plurality of personalized style transfers to the content template to generate the plurality of customized content.

3. The system of claim 2, wherein each of the plurality of clustered style transfers is associated with a distinct generative adversarial network, wherein each distinct generative adversarial network is trained on distinct training data.

4. The system of claim 3, wherein the distinct training data is associated with a cluster of similar visual impairments.

5. The system of claim 1, wherein each of the plurality of personalized style transfers corresponds to a distinct color mapping modification to the content template.

6. The system of claim 1, wherein the processor is further configured to transmit the selected one of the plurality of customized content to at least one other device.

7. The system of claim 1, wherein the content template includes a plurality of video frames, wherein the personalized style transfer is applied to each video frame of the content template.

8. The system of claim 7, wherein the personalized style transfer is applied to at least two video frames simultaneously.

9. The system of claim 1, wherein each generative adversarial network is a cycle-consistent generative adversarial network.

10. A method for dynamically modifying visual content, the method comprises:
 generating and presenting, with a processor, at least one visual impairment test to a user;
 receiving, with the processor, at least one response to the at least one visual impairment test from the user;
 generating, with the processor, a request for a plurality of customized content from the server based on the at least on response;
 querying, with a server, a memory database for a content template for the plurality of customized content;
 requesting, with the server, the plurality of customized content from a content generator based on the at least one response and the content template;
 applying, at the content generator, a plurality of personalized style transfers to the content template to generate the plurality of customized content based on the at least one response;
 presenting, with the processor, the plurality of customized content to the user;
 receiving, with the processor, a selection of one of the plurality of customized content from the user;
 comparing, with the content generator, the at least one response to a plurality of clustered style transfers,
 identifying, with the content generator, one of the plurality of clustered style transfers based on the comparison,
 generating, with the content generator, the plurality of personalized style transfers based on the identification, and
 applying, with the content generator, the plurality of personalized style transfers to the content template to generate the plurality of customized content.

11. The method of claim 10, further comprising:
 activating, with the processor, the selected one of the plurality of customized content, wherein the activating includes applying the personalized style transfer associated with the selected one of the plurality of customized content to other visual content at the processor.

12. The method of claim 10, wherein the at least one visual impairment test includes at least one color blindness test.

13. The method of claim 12, wherein each of the plurality of personalized style transfers corresponds to a distinct color mapping modification to the content template, wherein the distinct color mapping modification is associated with the at least one response to the at least one color blindness test.

14. The method of claim 10, wherein the at least one visual impairment test is generated upon determining that a user accessed certain content, wherein the certain content is one of a website, a television channel, or a video game.

15. The method of claim 14, wherein the content template includes a plurality of video frames, wherein the personalized style transfer is applied to each video frame of the content template.

16. The method of claim 15, wherein the personalized style transfer is applied to at least two video frames simultaneously.

17. The method of claim 10, wherein the content template is one of a video or an image.

18. The method of claim 17, wherein the video is live-action.

19. A system for dynamically modifying visual content, the system comprising:
   a mobile device; and
   a server;
   wherein the mobile device includes a processor, wherein the processor is configured to:
   generate and present at least one visual impairment test to a user,
   receive at least one response to the at least one visual impairment test from the user, and
   generate a request for a plurality of customized content from the server based on the at least one response;
   wherein the server includes a plurality of generative adversarial networks, wherein each generative adversarial network is associated with at least one corresponding style transfer, wherein the server is configured to apply a plurality of personalized style transfers to a content template to generate the plurality of customized content based on the at least one response.

* * * * *